(12) United States Patent
Esteve Tintó et al.

(10) Patent No.: US 11,921,110 B2
(45) Date of Patent: Mar. 5, 2024

(54) METHOD FOR PRODUCING AN ARRAY OF PLANAR MICROPARTICLES WITH SURFACE MOLECULAR MULTIPLEXING, RESULTING ARRAY AND USE THEREOF

(71) Applicant: CONSEJO SUPERIOR DE INVESTIGACIONES CIENTÍFICAS (CSIC), Madrid (ES)

(72) Inventors: Jaume Esteve Tintó, Barcelona (ES); José Antonio Plaza Plaza, Barcelona (ES); Marta Duch Llobera, Barcelona (ES); Núria Torras Andrés, Barcelona (ES); María Luisa Pérez García, Barcelona (ES); Juan Pablo Agusil Antonoff, Barcelona (ES)

(73) Assignee: CONSEJO SUPERIOR DE INVESTIGACIONES CIENTÍFICAS (CSIC), Madrid (ES)

( * ) Notice: Subject to any disclaimer, the term of this patent is extended or adjusted under 35 U.S.C. 154(b) by 0 days.

(21) Appl. No.: 18/085,462

(22) Filed: Dec. 20, 2022

(65) Prior Publication Data

US 2023/0118650 A1   Apr. 20, 2023

Related U.S. Application Data

(60) Continuation of application No. 17/181,958, filed on Feb. 22, 2021, which is a division of application No. 15/315,837, filed as application No. PCT/ES2015/070439 on Jun. 3, 2015, now abandoned.

(30) Foreign Application Priority Data

Jun. 5, 2014   (ES) ................. ES201430864

(51) Int. Cl.
| | | |
|---|---|---|
| *G01N 33/543* | (2006.01) | |
| *B01J 19/00* | (2006.01) | |
| *B82Y 30/00* | (2011.01) | |
| *G01N 33/48* | (2006.01) | |
| *G01N 33/58* | (2006.01) | |
| *G03F 7/00* | (2006.01) | |
| *B82Y 40/00* | (2011.01) | |

(52) U.S. Cl.
CPC .......... *G01N 33/5432* (2013.01); *B01J 19/00* (2013.01); *B01J 19/0046* (2013.01); *B82Y 30/00* (2013.01); *G01N 33/48* (2013.01); *G01N 33/582* (2013.01); *G03F 7/0002* (2013.01); *B01J 2219/00756* (2013.01); *B82Y 40/00* (2013.01)

(58) Field of Classification Search
CPC .............. G01N 33/543; G01N 33/48
See application file for complete search history.

(56) References Cited

U.S. PATENT DOCUMENTS

| | | | |
|---|---|---|---|
| 9,162,518 B2 | 10/2015 | Demierre et al. | |
| 9,372,397 B2 | 6/2016 | Mirkin et al. | |
| 10,683,493 B2 | 6/2020 | Clapés Saborit et al. | |
| 10,907,135 B2 | 2/2021 | Redondo Moya et al. | |
| 11,058,650 B2 | 7/2021 | Rodríguez De Fonseca et al. | |
| 11,298,416 B2 | 4/2022 | Grilló Dolset et al. | |
| 2005/0220887 A1* | 10/2005 | Herbert ................ | A61K 9/1647 424/489 |
| 2010/0021985 A1 | 1/2010 | Mason | |
| 2011/0128536 A1 | 6/2011 | Bond et al. | |
| 2012/0114559 A1* | 5/2012 | Singh ..................... | A61K 9/51 424/490 |
| 2016/0032480 A1 | 2/2016 | Ferrari et al. | |
| 2016/0256548 A1 | 9/2016 | Haber et al. | |
| 2020/0281897 A1 | 9/2020 | Pérez Simón et al. | |
| 2020/0345701 A1 | 11/2020 | López Serrano et al. | |
| 2021/0181189 A1 | 6/2021 | Esteve Tintó et al. | |
| 2021/0330662 A1 | 10/2021 | Alcázar González et al. | |
| 2021/0363501 A1 | 11/2021 | Redondo Moya et al. | |
| 2022/0135640 A1 | 5/2022 | Delgado Mora et al. | |
| 2022/0273785 A1 | 9/2022 | Grilló Dolset et al. | |

FOREIGN PATENT DOCUMENTS

WO   WO 2007024323 A2   3/2007

OTHER PUBLICATIONS

Okuda et al., Time-Programmed Dual Release Formulation by Multilayered Drug-Loaded Nanofiber Meshes, 2010, 143, 258-264. (Year: 2010).*
Torras et al., Suspended Planar-Array Chips for Molecular Multiplexing at the Microscale, Advanced Materials, Dec. 2015, 28, 1449-1454. (Year: 2015).*
Canelas et al., "Top-down particle fabrication: control of size and shape for diagnostic imaging and drug delivery," *Advanced Review: WIREs Nanomedicine and Nanobiotechnology* 1:391-404, 2009.
Chakrapani, "Processing and Characterization of Polymer Microparticles For Controlled Drug Delivery Systems," Dissertation, The Ohio State University: 1-92, 2006 (107 Pages).
Extended European Search Report, dated Jul. 18, 2018, for European Application No. 15803414.0, 4 pages.

(Continued)

*Primary Examiner* — Amy M Bunker
(74) *Attorney, Agent, or Firm* — Seed IP Law Group LLP

(57) ABSTRACT

A method for controlled production of an array of planar microparticles with the multiplexing of molecules on the surface thereof, intended to function as molecular sensors and/or actuators and a matrix (array) of microparticles, the surface thereof being printed with all of the molecular components required to provide the surface with functionality. Different molecular elements are multiplexed on the surface of each particle while they are supported on a substrate by means of a structural foot engraved below the particle. These microparticles can be released mechanically from the support on which they are produced using a controlled mechanical rupture method which is not chemically aggressive and therefore does not affect the molecules previously printed on the surface. The array and the particles contained therein offer great versatility in both chemical and/or biological applications.

25 Claims, 3 Drawing Sheets

(56) References Cited

OTHER PUBLICATIONS

Fernandez-Rosas et al., "Intracellular Polysilicon Barcodes for Cell Tracking," *Small* 5(21):2433-2439, 2009.

Huo et al., "Polymer Pen Lithography," *Science* 321:1658-1660, 2008.

International Search Report and Written Opinion, dated Sep. 14, 2015, for International Application No. PCT/ES2015/070439, 9 pages.

Jeon et al., "Fabrication of microparticles with controllable internal woodpile structures for highly efficient sensing applications," *RSC Advances* 2:2334-2339, 2012.

Kingsmore, "Multiplexed protein measurement: technologies and application of protein and antibody arrays," *Nature Reviews Drug Discovery:* 1-11, 2006.

Malainou et al., "Plasma-Assisted Nanoscale Protein Patterning on Si Substrates Via Colloidal Lithography," *The Journal of Physical Chemistry* 117: 13743-13751, 2013.

Malainou et al., Supporting Information, "Plasma-Assisted Nanoscale Protein Patterning on Si Substrates Via Colloidal Lithography," *The Journal of Physical Chemistry* 117: 13743-13751, 2013.

Merkel et al., "Scalable, Shape-Specific, Top-Down Fabrication Methods for the Synthesis of Engineered Colloidal Particles," *Langmuir* 26(16):13086-13096, 2010.

Murthy et al., "Silicon nanopillar substrates for enhancing signal intensity in DNA microarrays," *Biosensors and Bioelectronics* 24: 723-728, 2008.

Op De Beeck et al., "Hydrodynamic chromatography of polystyrene microparticles in micropillar array columns," *Journal of Chromatography A* 1217: 6077-6084, 2010.

Peer et al., "Nanocarriers as an emerging platform for cancer therapy," *Nature Nanotechnology* 2: 751-760, 2007.

Tasciotti et al., "Mesoporous silicon particles as a multistage delivery system for imaging and therapeutic applications," *Nature Nanotechnology* 3: 151-157, 2008.

Wang et al., "Fabrication of Two- and Three-Dimensional Silica Nanocolloidal Particle Arrays," *J. Phys. Chem. B* 107: 3400-3404, 2003.

Wu et al., "Fabrication of arrays of two-dimensional micropatterns using microspheres as lenses for projection photolithography," *Applied Physics Letter* 78(16): 2273-2275, 2001.

Xia et al., "Soft Lithography," *Angew. Chem. Int. Ed.* 37: 550-575, 1998.

Yuet et al., "Multifunctional Superparamagnetic Janus Particles," *Langmuir* 26(6): 4281-4287, 2010.

U.S. Appl. No. 17/926,278, filed Nov. 18, 2022.

U.S. Appl. No. 17/928,183, filed Nov. 28, 2022.

\* cited by examiner

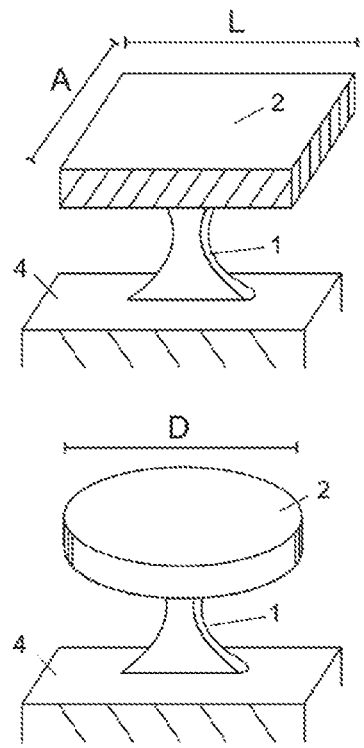
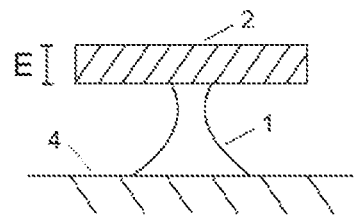
FIG. 1A  FIG. 1B
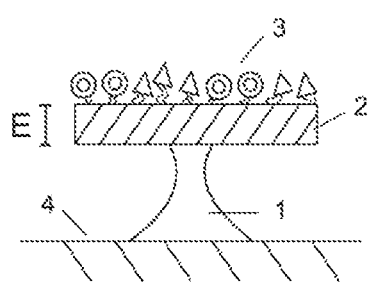
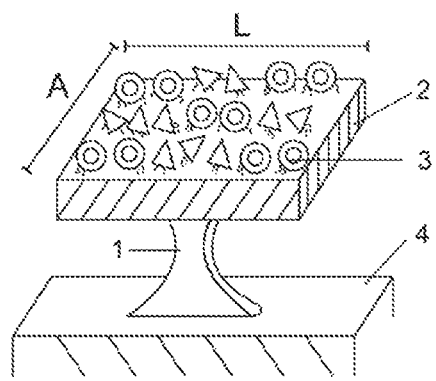
FIG. 2A  FIG. 2B

METHOD FOR PRODUCING AN ARRAY OF PLANAR MICROPARTICLES WITH SURFACE MOLECULAR MULTIPLEXING, RESULTING ARRAY AND USE THEREOF

CROSS-REFERENCE TO RELATED APPLICATIONS

This application is a continuation application of U.S. patent application Ser. No. 17/181,958, filed Feb. 22, 2021, which is a divisional application of U.S. patent application Ser. No. 15/315,837, filed Mar. 3, 2017 (now abandoned), which is the United States national phase of international Application No. PCT/ES2015/070439 filed Jun. 3, 2015, and claims priority to Spanish Patent Application No. P201430864 filed Jun. 5, 2014, the disclosures of which are hereby incorporated in their entirety by reference.

BACKGROUND OF THE INVENTION

Field of the Invention

The present invention is aimed at the application of new technologies for the manufacture of arrays of microparticles in the broad field of engineering. Due to the very nature of the array produced as well as the microparticles it contains, and which may be singled out by mechanical means, the area of application of this invention is very broad, encompassing the sectors of chemistry, cellular biology, medicine and pharmacology.

Description of Related Art

In the field of engineering and material science, a particle is understood to be any body with a micrometric or nanometric scale and having a mass, and which may be obtained naturally or artificially by means of physical and chemical methods. At present, the different existing techniques for obtaining micro- and nanoparticles may be classified into two large groups, based on whether they are produced directly in an individual manner, or whether they are produced in the form of an ordered matrix or array.

All of the techniques encompassed in the first of these two groups (individual particle manufacture) are based on two different types of approaches, called "top-down approach" and "bottom-up approach". The first of them is based on the production of a particulate material out of a "bulk" of material or larger structures, through progressive reductions in size (Dorian A. Canelas, Kevin P. Herlihy and Joseph M. DeSimone. *Wiley Inter. Rev. Nanomed. Nanobiotechnol.* (2009), 1, 4, 391-404). The bottom-up approach, on the other hand, consists of supramolecular chemical synthesis, which uses the chemical information contained in the different individual components (atoms or molecules) to get them to spontaneously group together into larger complex particles, by means of "self-assembly" processes (Wei Wang, Baohua Gu, Liyuan Liang and William Hamilton. *J. Phys. Chem. B* (2003), 107, 3400-3404). In recent years there has been increased scientific interest in the development of new polymer-based materials and compounds. By using chemical synthesis techniques, such diverse techniques have been developed as "flow-focusing", pulverization or microemulsion, which, combined with microfluidics, are also being used to fabricate particles, both simple and compound (K. P. Yuet, D. K. Hwang, R. Haghgooie and P. S. Doyle. *Langmuir* (2010), 26, 6, 4281-4287).

What is common to all of these self-assembly techniques is the direct production of large quantities of identical particles, made individually and at a low cost. The main drawback of these particle-manufacture methods is that strictly chemical methods must be applied for their functionalization, whereby either a total and single (identical) functionalization may be obtained for all of them, or a combination of two or more functionalizations, by using chemical substances, as long as these do not affect one another. It is a difficult and highly complex process due to the multiple incompatibilities that this entails (neither versatility nor discretization). The particles produced through the methods described above are usually used in the field of pharmacology and biomedicine as "drug delivery systems" (Tasciotti E., Liu X W, Bhavane R., Plant K., Leonard A. D., Price B. K., Cheng M. M. C., Decuzzi P., Tour J. M., Robertson F. and Ferrari M. *Nature Nanotechnol.* (2008), 3, 3, 151-157) and as "nanocarriers" (D. Peer, J. M. Karp, S. Hong, O. C. Farokhzad, R. Margalit and R. Langer. *Nat. Nanotechnol.* (2007), 2, 751-760); although they are also widely used, in the case of magnetic particles, as "magnetic separation bioprocesses", by means of magnetophoresis and electromagnetophoresis, as well as for research into new materials and compounds.

On the other hand, there is the set of ordered-particle-matrix manufacturing techniques, based on micro- and nanoelectronic fabrication processes. These techniques, both those based on conventional photo-lithography processes (M.-H. Wu and G. M. Whitesides. *Appl. Phys. Lett.*, (2001), 78, 16, 2273-2275) and those based on processes known as "soft-lithography" (Y. N. Xia and G. M. Whitesides. *Angew. Chem., Int. Ed.* (1998), 37, 551-557), such as micromolding, microcontact printing (MCP), among others, also allow for the simultaneous production of thousands of units (the concept of "batch processing"), in a controlled and low-cost manner, but with high adaptability for the use of materials as diverse as metals and polymers, including a large number of biomaterials, and the possibility of making changes between them. These processes give the designed particles a great deal of versatility, both in terms of shape and dimensions, and make it possible to simultaneously produce different types of particles. Although in some cases the manufacture process of this type of particles is more complex than those mentioned previously, these techniques make it possible to obtain particles with multiple surfaces, opening up the range to a wide variety of possible applications. Because of their ordered and controlled location on the surface of the substrate where they are produced, these particles make it possible to apply different types of functionalization on a single particle, in a localized manner within the same. The currently existing techniques for separating particles obtained through lithographic processes from the produced substrate, a concept known as particle release or individualization, require the use of methods based on the use of chemical agents that may be aggressive for the multiplexed molecules on their surface, as in the case of the "surface technique" (E. Fernández-Rosas, R. Gomez, E. Ibáñez, L. Barrios, M. Duch, J. Esteve, C. Nogués and J. A. Plaza. *Small* (2009), 5, 21, 2433-2439), where a sacrificial layer located between the particle and the substrate is etched with chemicals.

Multiplexed chips (understood as those chips that bring together in a single substrate—particle—various types of channels that can provide and receive different information, by means of each one of the functionalizations printed on their surface) made up of an ordered matrix of molecular elements, and with dimensions on the order of centimeters, for example "DNA chips", have been widely used in fields such as medicine and biology to identify, quantify and determine the workings of certain molecules (S. F. Kingsmore. *Nat. Rev. Drug. Discov* (2006), 5, 310-320). For cases in which small volumes of samples must be analyzed, the current technological solution is to produce particle suspensions in which each element is comprised by a sub-population of particles that differ from the other groups in that they have different anisotropic attributes (shape, dimensions, color, etc.). The lack of multiplexing on a single particle of the ones containing these suspensions, a characteristic multiplexed chips do offer, constitutes a significant limitation when it comes to analyzing small volumes (for example, the inside of a cell).

The present invention presents a new proposal based on the manufacture of an ordered matrix of planar microparticles with surface molecular multiplexing, whose geometry and dimensions may vary depending on their final application. The functionalization of its surface may be carried out in a controlled and ordered manner with a wide variety of molecules simultaneously, for example proteins and DNA. The microparticles are molded and prepared on a substrate that they are held on by a securing foot engraved below them, whereby they may be separated (released) through a method of controlled mechanical rupture without any chemical release techniques, as a result of the formation of this new structural element called a "foot" of the microparticle in the array.

This foot, which is similar to a column or pillar, acts as an element for securing these microparticles that make up the array or matrix to the substrate during the processes of molecular shaping and multiplexing on their surface, and likewise acts as an element that concentrates mechanical stress, making it the weakest point in the entire assembly. This makes it possible, should one wish to free the particles, to apply directed mechanical stress in order to break the foot in a controlled manner, without damaging the microparticles or the multiplexed molecules, since no chemical releasing agents are used which might affect the structure or function of said molecules. In other words, apart from being able to produce surface-functionalized microparticles, here, as opposed to in other known methods, it is possible to individualize the microparticles in the array by means of a chemically non-aggressive method, i.e. one which does not require the use of chemical agents that might damage the integrity of the microparticle or affect its prior molecular functionalization. Once released, said microparticles, as with the array, are able to act as sensors or actuators of different activities, both chemical and biological, brought about in the medium where they are found, for instance certain chemical reactions or variations in physical parameters such as temperature and pH, among others.

SUMMARY OF THE INVENTION

The invention described herein relates to an array of planar microparticles with surface molecular multiplexing prepared from a starting material deposited or grown on a substrate acting as a support, whose mission is to act as a molecular detector, sensor and/or actuator in a sample medium which may be chemical or biological. Specifically, the array is manufactured with microelectronic technology, and the functionalized microparticles that it contains are characterized in that they have dimensions which may be comprised in the range of 1 µm to 100 µm, as required by their final application, it being possible to prepare them on the substrate in large quantities, with well-defined shapes and dimensions. Due to its size (micrometric) and its surface functionalization, the microparticle array which may be obtained using this method offers great versatility with regards to specific applications, and may be used both in chemical and biological media, always for scientific and technical purposes.

The foot that is engraved under the starting material of the microparticle (which corresponds to the upper portion of the support) acts as a structural element, individually joining each microparticle to the substrate during the manufacturing and molecular multiplexing processes, and allowing the microparticles to be placed on the substrate in an ordered manner. Moreover, as a result of the formation of this new structural element, the microparticles may be separated from the substrate and individualized in a controlled manner by applying directed mechanical stress, for instance transverse mechanical stress, a chemically non-aggressive method which therefore respects the integrity of the surface-multiplexed molecules. Thus, all of the prior functionalization carried out is preserved unaltered, allowing the microparticles to be released subsequent to functionalization.

The great industrial advantage of this proposed method resides in the possibility of manufacturing surface-functionalized microparticles in series on a substrate, specifically on a foot that acts as a support and enables the use of parallel printing methods for the simultaneous molecular functionalization of all of the microparticles, for example in the same way. Moreover, in a preferred embodiment of the invention, the foot formed under the starting material that gives rise to the microparticles during the manufacturing process enables them to be released or individualized by mechanical separation from the foot by breaking the latter. Due to its own design and geometry, which is similar to a column or pillar that sustains the microparticle, this foot becomes the most fragile area in the structure, concentrating the mechanical stress and ensuring the fracture area should one wish to release the microparticles for individual use.

Ideally the foot should have a variable (non-constant) cross-section, i.e. with two different areas such that one of them is narrower, the narrowest area of the cross-section preferably being in the center. Thus, the foot offers the resistance needed to sustain the microparticle during the functionalization process, and at the same time has a narrower area where the majority of the mechanical stress is concentrated in the case of controlled release. In a particular embodiment, the foot may also have a constant cross-section, so long as said cross-section is smaller than the cross-section of the microparticle itself, preferably less than or equal to 50% of the size of the cross-section of the microparticle.

Due to its design and geometry, both the foot and the microparticles in the array may be formed out of the same material, although it is preferable for the foot to be made with fragile, non-ductile materials, thereby further facilitating the controlled rupture thereof.

As such, the first object of the present invention is the method itself for producing an array of planar micrometric particles with functionalized surface, said method comprising the following stages:
 a) preparing a layer of a microparticle starting material (also called structuration layer) on top of a substrate that serves as a support, typically a silicon sheet, although it may be any other material that is equally suitable for this purpose; said layer of microparticle starting material may be of a typical microelectronics material, such as polycrystalline silicon, silicon oxide, silicon nitride, gold, platinum, aluminum, etc.;

b) shaping the microparticles in the structuration layer previously prepared on top of the support by means of common lithography-based microelectronics techniques, with which the geometry and lateral dimensions are defined, and engraving techniques with which the thickness is defined after preparing the layer;

c) the key point in the method is the formation of a foot in the upper part of the substrate that is found below the previously molded microparticles, such that each foot sustains a microparticle. The foot of each microparticle is formed by engraving said upper part of the substrate, wherein said engraving may be carried out by means of common microelectronics techniques. In this way, the feet of the microparticles are prepared to be sufficiently stable from a mechanical point of view in order to sustain them during the subsequent stage of molecular functionalization on the surface of the microparticles, but also fragile enough to allow them, if so desired, to be broken in a controlled manner by applying directed mechanical forces, thus allowing the foot to be broken and the microparticle to be released from the array. This is why it is advisable for the foot to be produced from a fragile material such as silicon; and d) functionalizing the surface of the microparticles that are supported by the feet by means of at least one molecular component, preferably by means of a method that makes it possible to functionalize a large number of microparticles in parallel, by way of example, soft-lithography techniques such as micro-contact printing (MCP), dip-pen nanolithography (DPN), polymer-pen lithography (PPN) or nano-imprint lithography (NIL).

Basically, the substrate that acts as a support for the manufacture of the microparticles is covered in a layer that defines the original material of said microparticles that will subsequently be molded, and which may be selected from the group of materials consisting of: silicon and derivatives thereof (silicon nitride or silicon oxide, polycrystalline silicon), gold, platinum, aluminum, copper, nickel, cobalt or chromium; metal oxides; and silicates or silicides of compatible metals such as tantalum, iron or aluminum. This layer is structured or molded upon the substrate to define the desired shape of the microparticles, and subsequently the foot located below them is structured or defined.

The foot carries out a dual function. On the one hand, it keeps the microparticle joined to the substrate throughout their manufacturing process, as well as during the subsequent functionalization steps, ensuring its position at all times. On the other hand, since it is the weakest and most fragile part of the whole structure, it acts as a stress-concentrating element, enabling it to break should one wish to separate or release the microparticles from the matrix.

After shaping or molding the foot of the microparticles by means of partial engraving (i.e. only in part and not the entire cross-section constantly, because a column or pillar shape is preferable), the surface of said microparticles is functionalized with the various molecular elements that have been selected (such as organic compounds, polymer chains, proteins, DNA, etc.). This action is carried out in parallel, although given that the surface of the substrate contains various microparticles, the functionalization in parallel may be repeated in series in order to endow the particles with more than one functionalization; or, it is also possible to repeat the printing of the same substance several times. Thus, thanks to functionalization, microparticle multiplexing is achieved in such a way that a single molecular element printed more than once or more than one different molecular element is located in an orderly way on the surface of each one of the microparticles, unlike the planar chips of molecular matrices, with dimensions on the order of centimeters, that do not analyze small volumes, which could be, for example, a cell of an ex vivo and/or in vitro sample, and unlike the suspensions of known micro-nanoparticle sub-populations, where each sub-population has a single molecular element but does not allow for the multiplexed analysis of a same microparticle. The embodiment of an array of molecularly multi-functionalized microparticles on the order of microns, as is the case of the present invention, also allows for the multiplexed molecular analysis in small volumes.

The array of microparticles, after its functionalization, can be stored in a dry place.

A second object of the present invention relates to the array of planar microparticles with functionalized surface itself obtainable by using the method described above, as well as the microparticles themselves which can be separated from the matrix by means of controlled mechanical disruption of the foot. Preferably, a suspension of these microparticles can be prepared.

The array of microparticles, as well as the microparticles themselves that are functionalized and released from the support, and the suspension that can be prepared with the microparticles can act thanks to their properties as molecular detectors, sensors and/or actuators. In other words, the invention also has a third object which covers the use of these products as sensors, actuators or detectors of physical, chemical and biological parameters simultaneously or separately in a medium or sample.

The present invention is based on the relative observation of the array of microparticles, which are manufactured on the support with micrometric dimensions (physical lateral dimensions preferably comprised between 1 μm and 100 μm, and preferably with a thickness of between 20 nm and 5 μm) and duly functionalized molecularly through certain features outlined in a selective and controlled way on its surface.

DESCRIPTION OF THE DRAWINGS

FIG. 1A is a perspective view of FIG. 1B is a cross-sectional view of a representation of two possible configurations of microparticles in the array obtained through the method described, one in the shape of a parallelepiped with a width A, length L and thickness E, and the other in the shape of a circle or a disk, with a diameter D and thickness E, according to the invention, where (1) represents the material that makes the foot, (2) the microparticle and the substrate (4).

FIG. 2A is a cross-sectional view and FIG. 2B is a perspective view of a representation of a possible microparticle configuration on the support in the array, where its upper surface has been coated, in a localized manner, with different molecular elements designed for its functionalization (3).

DESCRIPTION OF THE INVENTION

Figure 3A:
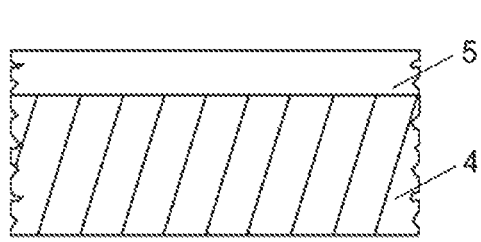
FIGS. 3A-3H show a manufacturing process of the array of microparticles based on microelectronic technology, photo-lithographic processes and layer etching, according to Example 1, wherein after producing the microparticle matrix, these microparticles are released and prepared in suspension. A straight section that shows the manufacturing process of a microparticle, with a substrate that is mainly a silicon sheet (4) that acts as a support, upon which there is a layer (5), typically made up of polycrystalline silicon, silicon oxide, silicon nitride, gold, platinum, aluminum or chromium, which constituted the original material that became the microparticles (2) (FIG. 3A). To define the microparticles, a photo resin layer (6) was deposited on said layer of original material of the microparticles (FIG. 3B), which was then partially eliminated from specific areas (7), forming a structured photo resin layer (8) that contained the geometry and lateral dimensions of the microparticles to be produced (FIG. 3C). Said microparticles were formed (structured) by etching the layer of their starting material (5) in the uncovered areas (7) where the layer of photo resin (6) had previously been removed, thereby forming the body of the microparticle(s) (2) (FIG. 3D). Afterwards the silicon substrate (4) was engraved immediately below the microparticles (2) to form the foot (1) (FIG. 3E). The remaining photoresin (8) was removed in the upper part of the microparticles (2) (FIG. 3F). After this the molecular functionalization of the microparticles was carried out with more than one molecular element (3) (FIG. 3G). Lastly, the functionalized microparticles (2) were released from the substrate (4) by means of controlled rupture, and were gathered in an aqueous medium, in this example, previously filtered de-mineralized water, thus producing the microparticle suspension (9) (FIG. 3H).
Figure 3B:
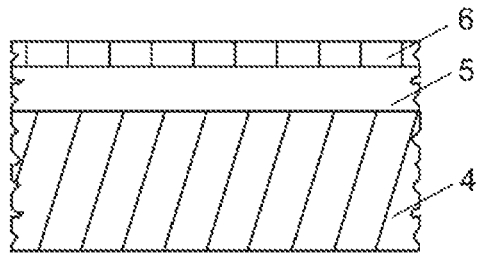
Figure 3C:
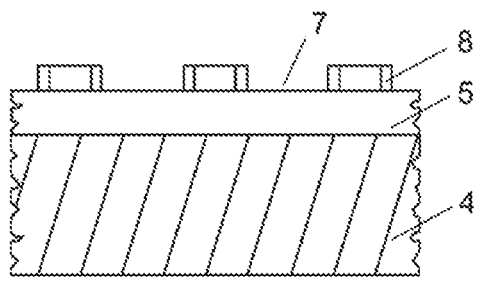
Figure 3D:
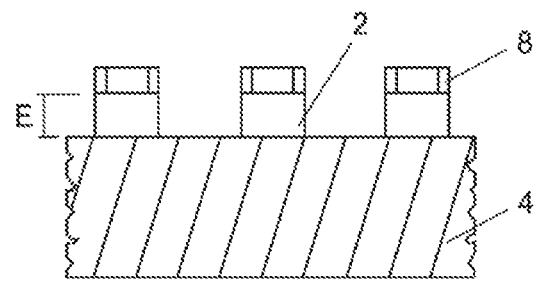
Figure 3E:
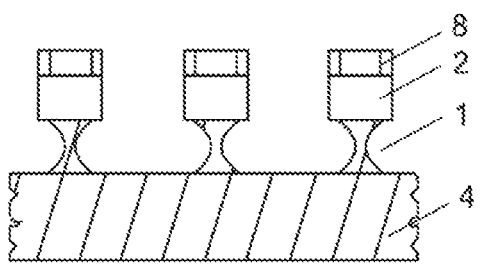
Figure 3F:
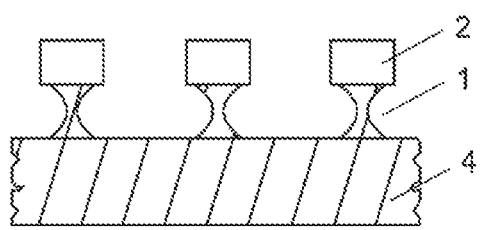
Figure 3G:
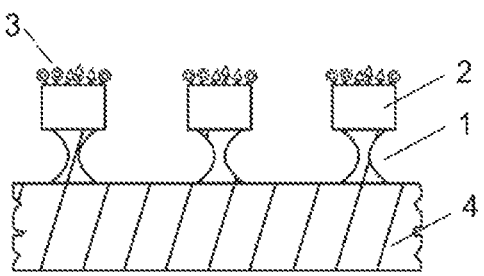
Figure 3H:
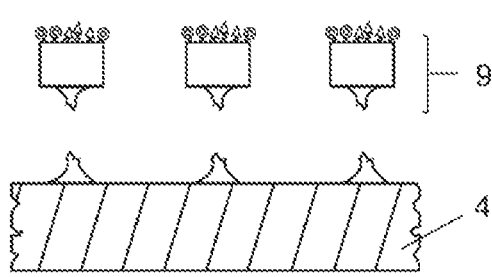
Figure 4:
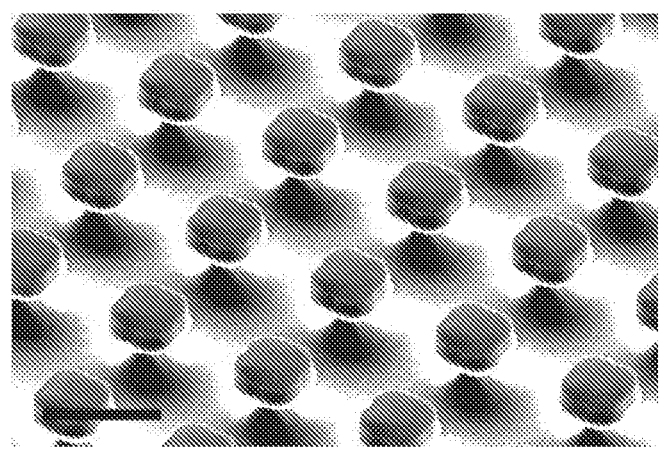
FIG. 4 is a scanning electron microscope image showing an example of producing the array of parallelepiped-shaped silicon oxide microparticles (dimensions of 3 µm×3 µm×1 µm) in accordance with Example 1—Section A, wherein one may easily make out the microparticles arranged in array and anchored to the substrate by means of a foot. Scale bar=5 µm.
Figure 5:
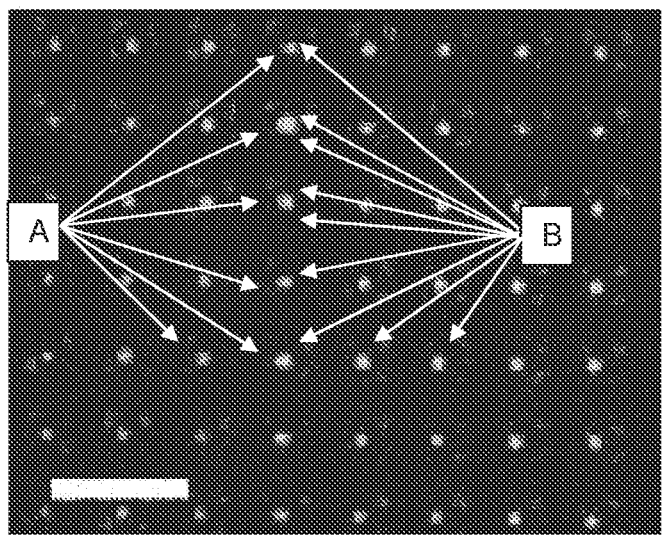
FIG. 5 is an optical fluorescence image showing an example of surface functionalization of the microparticles by means of the polymer-pen lithography technique, in accordance with Example 1—Section B. In this case, multiple printings with two different inks are shown, namely WGA lectin conjugated with the fluorophore Streptavidin Texas Red® (red, ink marked with the letter B in the figure and visualized with darker gray shading on a black background) and the protein BSA conjugated with the fluorophore Neutravidin Oregon Green® (green, ink marked with the letter A in the figure and visualized with lighter gray shading) prior to being functionalized with the antibody Goat Anti-Rabbit IgG conjugated with the marker AMCA and a third ink (blue, not shown in the figure). In this case, the printed pattern was dots. Scale bar=10 µm.
Figure 6:
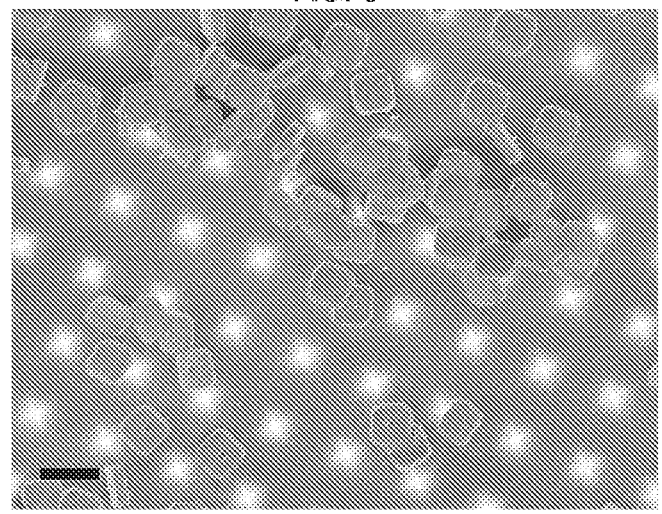
FIG. 6 is a scanning electron microscope image showing several microparticles following their mechanical release from the substrate by means of controlled mechanical fracture of the feet in accordance with Example 1—Section C. Scale bar=5 µm.

As mentioned in the foregoing section, the foot is produced through molding by engraving the upper part of the substrate, which is in direct contact with the lower part of the layer of microparticle starting material. In a particular embodiment of the invention, the substrate is formed by a single material, most preferably a silicon sheet, although it may be another suitable type of substrate that offers mechanical support for the fabrication of the microparticles, for example borosilicate glass (commonly known by its commercial name, Pyrex or Duran) or soda-lime-silica glass, among others. Nevertheless, the invention is not limited just to these support materials, since any person skilled in the art will know what types of materials are suitable and may fulfill the intended function; basically, this includes all materials that meet the following conditions:

be resistant to the thermal processes of depositing, evaporating and growing layers;

be stable at ambient temperature;

be resistant to certain chemical agents (compounds in liquid or gas phase) in order to enable the structuration/engraving/processing in general of the layers in them without affecting the substrate (even though sometimes they need to be protected, since the chemical agents tend to be quite aggressive); and having the ability to itself be structured/engraved (wholly or partially). This would be the case in which the foot of the microparticles is produced out of the substrate itself.

Thus, the substrate must first and foremost act as a support, and therefore must be rigid enough to support the structures, and, while these structures are being processed, it must maintain its integrity without breaking. Furthermore, in this preferred embodiment, it must also allow for the foot to be formed on its upper part, which is in contact with the microparticle starting material. In a particular embodiment of the invention the support or substrate may be made of the same material used for the microparticle starting layer. For example, microparticles can be manufactured on a substrate that is a silicon sheet with a silicon foot (i.e. it is engraved into the substrate itself), wherein the particles have been molded in a polysilicon layer; this enables the possibility of subsequently carrying out thermal doping processes to provide the microparticles with charges.

In another particular embodiment of the invention that is an alternative to the preceding one, the substrate is formed by at least two materials, such that it contains a second material in its structure that is located in the upper part in the form of a layer, where it has been deposited or grown. In this way, the foot can be molded by engraving this second material contained in the upper part of the substrate. If the substrate contains a second material in the upper part of its structure, where the feet will be engraved, this second material may be the same material used to produce the microparticles themselves, or a different material, preferably one that is more fragile and less ductile than the structuration layer so as to guarantee that it behaves correctly under the subsequent breaking stress, for instance polycrystalline silicon. For example, it is possible to use a silicon substrate (sheet) only as the support of the layer that will be used as a starting material for the foot and for the microparticles, without intervening in any way in the manufacture of the devices defined in it. Silicon, though not the only option, is highly recommendable because it is the microelectronics material par excellence given its compatibility with most processes and resistance to temperature changes and chemical agents.

Likewise, the preparation in stage a) of the structuration layer, which is the same thing as the layer constituting the material that gives rise to the microparticles, can be carried out by depositing it or by growing it on top of the substrate itself. The materials that the structuration layer can be made of may be selected from the group consisting of: silicon and derivatives thereof (silicon nitride or silicon oxide, polycrystalline silicon), gold, platinum, aluminum, copper, nickel, cobalt, chromium, metal oxides, and silicates or silicides of compatible metals such as tantalum, iron or aluminum. This layer can be deposited or can be grown by any method used in microelectronics: thermal growth, chemical vapor deposition, sputtering, evaporation, or other common methods used today. The method selected for this will be determined by the choice of materials to use.

To guarantee good mechanical behavior of the entire structure (microparticle plus foot), it is preferable for the material chosen for the structuration layer and the material of the substrate that will be engraved into a foot, whether the substrate is made of one material or contains a second material in its upper part, to have a relationship between its rupture limits greater than or equal to one ($L_{rupt\_part}/L_{rupt\_foot} \geq 1$). This not only secures the particles during functionalization, but also ensures that the foot is more fragile than the microparticle and is therefore more vulnerable to rupture when mechanical stress is applied in cases where one wishes to free said microparticles from the substrate in a controlled manner (facilitate their release). Nevertheless, if the final application so requires, the structuration layer and the second material that contains the substrate in its upper part can be manufactured from the same material, since their own design and geometry enable this.

The method of manufacturing the microparticles based on microelectronic technology makes it possible to define its dimensions preferably by using photo-lithographic techniques, said techniques being commonly used in the field of microelectronics. The use of photo-lithographic techniques makes it possible to form microparticles into specific shapes and dimensions, chosen with technical criteria, preferably being identical to one another, although this technique also allows for the manufacture of groups of microparticles that are identical to one another but different from other groups in the same array. The micrometric particles in the array produced by means of the described method may preferably have dimensions comprised between 1 μm to 100 μm, both limits included, on the plane of the microparticle. Also preferably, the microparticles may have a thickness comprised between 20 nm and 5 μm, both limits included. The microparticles may have varying geometries, for instance a parallelepiped or circular shape, although these shapes shall not limit the invention.

The shape of the foot under the microparticle can be defined through any engraving technique that allows for partial elimination, just underneath each microparticle, of the material forming said foot, whether it is the only material making up the substrate or the second material that said substrate may contain in its upper part. In this way said element can be given a preferred shape of the column or pillar type, with a cross section having two differentiated portions, one narrower than the other, to force the mechanical stress to concentrate there, or with a cross section that is uniform throughout its length but smaller than that of the microparticle itself, preferably less than or equal to 50% of the size of the latter's cross section. The technique used to form the feet should preferably be physical etching (dry reactive etching) or chemical etching (wet), with lateral etching, depending on the material or materials present in the structures (in the shape of both the microparticle and the foot) and which in turn makes it possible to produce a foot with a constant or varying cross section, whichever is best for the required application.

In turn, the microparticles may contain one or more classes of molecules organized into monolayers in localized areas, which allow them to have several simultaneous uses, and in turn to carry out specific measurements or observations of one or several parameters and/or activities inside the medium where they are found. More specifically, said chemical functionalization may comprise several molecules of natural or synthetic origin, with chemical and/or biological activity, which include, but are not restricted to, simple organic compounds, polymers, peptides, proteins, nucleotides and nucleic acids. The molecules can be deposited on the upper face of the microparticles preferably using techniques from the field of micrometric- and nanometric-scale molecule printing, such as microcontact printing, dip-pen nanolithography or polymer-pen lithography.

As explained previously, it may be possible to release the microparticles from the array produced by means of the method described. In this particular embodiment of the invention, after stage d) for functionalization of the surface of the microparticles, the described method further comprises:

e) proceeding to break, in a controlled manner, the feet that support the microparticles by applying directed mechanical loads, in order to separate them from the substrate (individualize them). These loads may be applied by means of a variety of techniques, such as rasping the foot; applying an adhesive substance on the already functionalized surface of the microparticles and subsequently pulling it off, then dissolving the adhesive in media that do not affect the molecular functionalization of the microparticle; cryofracture, etc.

In this way, by applying directed mechanical stress, the feet can be broken in a controlled manner, for example with a clean cut, in order to release the microparticles from the substrate of the array without breaking or damaging them, preserving intact the functionalization that was previously applied to them, since it is a completely physical method that is not chemically aggressive.

Preferably, the mechanical rupture of the feet to individualize the microparticles that they sustain may be carried out by means of a directed cut, applying a controlled lateral force strong enough to break the foot. Said cut may be done with a micro-tool appropriately designed for this purpose, comprising a sharpened flat-tipped spatula having micrometric dimensions. In another preferred embodiment, the mechanical rupture may be carried out by means of cryofracture, freezing the entire structure of the array (the substrate with functionalized microparticles and their respective feet), which comprises: wetting the substrate with a solution such as a phosphate-buffered saline solution (PBS) with a content of 0.05% of Tween 20 solution (PBS-T); submerging the entire structure in liquid nitrogen until freezing the solution; re-wetting in the same way and re-freezing with liquid nitrogen; then finally applying a force or movement of leverage with a gripper or similar element until breaking the foot. The frozen solution that contains the microparticles is left to melt at ambient temperature in order to release them. In another preferred embodiment, an adhesive substance may be deposited on top of the chemically functionalized microparticles, for instance a layer of a polymer matrix such as Fluoromount®, in liquid phase so that it can enter even underneath the microparticles, which partially hardens after polymerizing. This substance is an aqueous-based biological mounting medium that is commonly used to cover tissues containing fluorescent markers, for subsequent inspection in optical microscopes such as confocal microscopes, and fluorescence microscopes, including scanning and transmission electron microscopes (SEM and TEM). At this point, said layer of the polymer matrix can be manually separated from the substrate, carrying along with it the microparticles and breaking the feet as it separates them, after which this hardened layer can be dissolved in a medium which does not affect the chemical functionalization, for example in an aqueous medium, in order to eliminate it from the surface of the microparticles.

Likewise, in a more preferred version of the foregoing embodiment, the method further comprises:

f) gathering the functionalized and separated (or individualized) microparticles in a suspension medium, which may be any medium that does not affect the chemical functionalizations.

Thus, the microparticles, once they have been separated from the substrate by mechanical means, can be kept for storage in a suspension in an aqueous medium that may be an acid, neutral or base, it matters not which, as required by the type of functionalization carried out.

Through the fabrication method it is possible to produce an array of planar microparticles with surface molecular multiplexing. Likewise, in the particular embodiment in which the feet of the structure are mechanically broken, these same functionalized microparticles are obtained but individualized. In an more preferred embodiment, a suspension of these microparticles is achieved, according to the aforementioned. Any of those products, array, microparticle(s) and microparticle suspension may be used to analyze, by way of example, "chemical parameters", which are all the measurable chemical magnitudes, such as the pH or the redox (oxidation/reduction) potential. What is more, it may be used to simultaneously measure several "biological parameters", thus referring to any magnitude that proves the presence of specific biological compounds, or the action thereof in the medium in which the microparticles are found. Said parameters may be ion concentration in solution, the activity of a specific enzyme, the presence of proteins and/or ligands, even the study of DNA, among others. These parameters in a sample medium may be measured by means of the signal emitted by one or more microparticles of the array, by one or more released and individualized microparticles or by one or more individualized microparticles and in suspension that is added to the sample medium. The sample medium in which the array may be used, the individualized microparticle or microparticles or the suspension thereof may be used as a sensor, actuator or the like, may be any chemical or biological medium, for example, an in vitro cell sample. In fact, a single cell may be a suitable sample medium in which to measure specific parameters due to the functionalization of the microparticles, which means that, in this embodiment, a microparticle may be separated from the array to insert it into the cell.

It must be noted here that if the array, the individualized microparticles or the microparticle suspension are used as actuators, these may also serve in the more preferred embodiment for substance vehiculation, such as for example, drugs or specific reagents. As such, in some of the examples of the use of the array or the microparticles thereof once individualized through the methods described above, it must be noted that they may be used in the field of pharmaceuticals and biomedicine as drug transport systems or drug delivery systems.

EXAMPLES

Example 1: Producing an Array of Planar Microparticles, Each One Functionalized with Three Different Proteins and Produced Through the Method Proposed in the Present Invention, and Release of Functionalized Microparticles to Produce a Suspension The aim of this example is to demonstrate the possibility of manufacturing an array of planar microparticles, with dimensions of 3 μm×3 μm×1 μm functionalized with three types of different molecules. In this particular embodiment, the method for placing the molecules on the planar surface is based on the polymer-pen lithography technique. Three different proteins have been printed using this technique.

A—Producing the Microparticles.

To produce microparticles, a monocrystalline silicon sheet with crystallographic orientation (100) with a diameter of 100 mm and thickness of 525 μm was taken. A thermal silicon oxide was thermally grown on it at 1100° C. This grown material was used for the subsequent structuration or molding of microparticles. Then, as set forth in the paragraphs of the Detailed Description, the photolithographic process is carried out, that is, the definition of the structures of the microparticles. To do so, 1.2 μm of positive photoresin (HiPR 6512) was deposited on the sheet. Using a glass grid as a mask on which the geometry of the microparticles was defined in chromium, the resin was irradiated with monochromatic light (wavelength 435 nm). For the specific embodiment of this Example of the Invention, square geometric shapes were arranged on the plane, which were 3 μm long and separated from one another by 3 μm. After irradiating the photoresin for 5 to 8.5 s, it was partially removed in a developer solution ODP 462 so that resin only remained in areas of the silicon oxide layer that subsequently defined the microparticles. Then, the remaining resin was annealed at 200° C. for 30 min in order to increase the strength thereof against subsequent etching. The following process consisted of carrying out vertical etching on the entire surface, in order to engrave the silicon oxide layer in the area that was not protected by the resin. To do so, a dry reactive ion etching equipment was used, using a mixture of $C_2H_6$ and $CHF_3$. This etching ended when the silicon sheet was reached. After this step of the process, the microparticles were already well defined but still joined to the silicon sheet. In the following stage of the manufacturing process, an isotropic etching of the silicon sheet was carried out, using the silicon oxide structures as a mask, along with the remaining resin layer, in a deep reactive ion etching (DRIE) process. To do so, $SF_6$ and $C_4F_8$ gases were used. This process laterally etched 1.3 μm, from all sides, the silicon located below the silicon oxide microparticles for the formation of the feet the held the microparticles joined to the silicon sheet during the chemical functionalization process. Lastly, the photoresin used as a mask was removed until the microparticle surface was clean of organic compounds, leaving the microparticles ready for their molecular functionalization and subsequent rupture to gather and suspend them.

B—Functionalization of the Surface of the Microparticles

As an example of functionalization of the surface of the microparticles described above, the technique referred to as polymer-pen lithography was applied. This technique (Fengwei Huo, Zijian Zheng, Gengfeng Zheng, Louise R. Giam, Hua Zhang and Chad A. Mirkin, *Science* (2008) 321, 1658-1660) combines the possibility of printing or assembling molecular monolayers on a large surface, characteristic of the microcontact printing technique, with the accuracy of individualized printing using the dip-pen nanolithography technique.

This technique previously required the manufacture of a mold or stamp made of soft polymeric material to transfer the molecules to the surface of the sample. In this exemplary embodiment, polydimethylsiloxane (PDMS), an organic polymer-based silicon in liquid state, was used, the components of which (a curing agent and the base elastomer) are mixed in a ratio of 10:1 by weight and are cured at a temperature between 60° C. and 100° C. for a period of time that may vary between 45 min and 120 min, depending on the hardness desired. To manufacture the mold for the PDMS stamp, another silicon sheet was used where a 1 μm layer of silicon oxide is thermally grown at 1100° C. A photo-lithography process, such as the one described above was used, but with an inverted mask compared to the one used to define the microparticles (where before there was resin, now there is not, and vice versa). Similarly to the previous embodiment, the silicon oxide layer was engraved through the existing mask and the remaining resin was subsequently removed. Once in this state, an anisotropic KOH etching was carried out, with which inverted pyramids were defined in the area where there was no silicon oxide. These pyramids enabled the subsequent production of the polymer points. Due to the use of the same mask, but inverted, it is possible to produce a polymer point for each microparticle. Therefore, in this specific example a matrix of square-based inverted pyramids, of 3 μm by 3 μm, separated by 3 μm, with a depth of 2.12 μm. Once the mold has been obtained, a surface treatment was carried out with fluorosilane trichloro-1,1,2,2-tetrahydroperfluorooctylsilane at 97% to prevent the polymer from adhering to the mold. In this state, liquid PDMS was deposited on this mold and after the curing thereof, the PDMS stamp was removed.

This stamp was used to transfer the absorbed molecules to the point of the pyramids on the surfaces of the microparticles. In order to put the molecules on the PDMS mold, the so-called inks are used. These inks are solutions that may contain any type of substance that one wishes to print; from organic molecules, such as for example fluorescent or fluorophore markers, as well as biomolecules such as single-strand DNA, proteins, etc. depending on the subsequent application thereof. In this exemplary embodiment, three types of different inks were used: i) wheat germ agglutinin (WGA) lectin conjugated with the Streptavidin Texas Red® fluorescent marker (SAV-TR) in red; ii) bovine serum albumin (BSA) protein conjugated with the Neutravidin Oregon-Green® fluorescent marker (NAV-OG) in green; iii) Goat Anti-Rabbit antibody IgG conjugated with the AMCA (7-Amino-4-methyl-3-coumarinylacetic acid) in blue, respectively. As a process control and to visualize the results obtained, a fluorescence microscope was used.

C—Mechanical Release of the Microparticles Previously Functionalized by Means of Controlled Mechanical Fracture.

To release the printed microparticles of the silicon sheet, a drop of Fluoromount® mounting medium is deposited on the sheet, forming a layer that homogeneously covered the microparticles of the sheet. The medium was left to polymerize at room temperature for 1 hours, creating a solid layer that covered the microparticles. This layer is mechanically separated from the sheet, taking the microparticles that had been broken at the feet with it. This method prevents the deterioration of the molecules previously printed since the medium was chemically inert.

The polymerized layer that is separated from the sheet with the separated microparticles was able to be stored in this state, for the subsequent use thereof in suspension. In order to obtain the microparticles in suspension, the separated layer was dissolved in an aqueous medium, such as for example, de-mineralized water or buffer solutions.

Example 2: Molecular Recognition of Proteins: Demonstration of the Use of the Suspension of Microparticles with Molecular Multiplexing Prepared in Example 1 as Sensor and/or Actuator In order to demonstrate that the functionalized molecules on the surface of the microparticles continue to be active (they maintain their integrity and functionality and therefore, are able to react with different elements of the medium) after being immobilized and once the microparticles have been released from the array substrate by means of controlled rupture of the feet, an antibody binding assay was carried out. For this assay, Goat anti-WGA IgG was chosen as the primary antibody and anti-Goat IgG (H+L) conjugated with the fluorescent marker AMCA (7-Amino-4-methyl-3-coumarinylacetic acid) in blue was chosen as the secondary antibody. These antibodies were orderly incorporated (in first place the primary antibody and then the secondary antibody) in an aqueous medium, following the standard methods of these assays, wherein the suspension of microparticles had previously been incorporated, giving rise to the recognition of proteins by the primary antibodies and the resulting bonding of both molecules (primary and secondary antibodies) to said proteins.

As a result, the expected sums were noted in the fluorescence emissions of the proteins previously printed on the microparticles due to the correct addition of emissions of the fluorescent markers present in both the proteins and the antibodies; perfectly visible changes using a conventional fluorescence microscope and that shows that the molecular recognition centers of the proteins continue to function. Said changes were the following:

a) the fluorescence signal in red emitted by the WGA lectin conjugated with SAV-TR was added to the emission in blue of the secondary antibody conjugated with AMCA, creating a representation in magenta, b) the fluorescence signal in green emitted by the BSA protein conjugated with NAV-OG was added to the emission in blue of the secondary antibody conjugated with AMCA, creating a representation in cyan, c) the Goat Anti-Rabbit IgG antibody conjugated with AMCA that initially emitted a blue fluorescence signal, continued to emit in said color.

As a control of the functionality of the multiplexing system, said immunoassay was successfully carried out with the manufactured array, that is, between steps B and C of Example 1 of the embodiment (after the manufacture and functionalization of the microparticles and before their release from the substrate), in order to demonstrate that the molecule multiplexing system by means of the polymer-pen lithography technique followed by the mechanical release system of the microparticles did not affect the correct activity of the molecules.

The invention claimed is:

1. A method for producing a plurality of individual chemically functionalized microparticles, the method comprising:
   (a) preparing a layered structure including, in order from top to bottom:
      (i) a structuration layer having a top structuration layer surface and a bottom structuration layer surface, and
      (ii) a multi-layer substrate comprising:
         an upper substrate layer having an upward facing first substrate surface, that is attached to the bottom structuration layer surface of the structuration layer, and a downward facing second substrate surface below the first substrate surface; and
         a lower substrate layer having an upward facing third substrate surface, attached to the second substrate surface of the upper substrate layer, and a downward facing fourth substrate surface below the third substrate surface, wherein:

the upper substrate layer comprises an upper substrate material, and the lower substrate layer comprises a lower substrate material;

the structuration layer comprises a structuration material selected from the group consisting of polycrystalline silicon, silicon oxide, silicon nitride, gold, platinum, aluminum, copper, nickel, cobalt, chromium, metal oxides, tantalum silicate, iron silicate, aluminum silicates, tantalum silicide, iron silicide and aluminum silicide;

the upper substrate material and the structuration material are different materials; and the upper substrate material and the lower substrate material are different materials;

(b) shaping the top structuration layer surface of the structuration layer using a first microelectronic lithography technique to obtain a shaped structuration layer having an uncovered area, and engraving the uncovered area of the shaped structuration layer to obtain a plurality of engraved structuration layers each having a defined thickness, wherein:

each of the plurality of engraved structuration layers is attached to the first substrate surface of the upper substrate layer via an engraved bottom structuration layer surface, each of the plurality of engraved structuration layers has an engraved top structuration layer surface, and the engraving of the shaped structuration layer creates an uncovered area of the upper substrate layer;

(c) engraving the uncovered area of the upper substrate layer using a second microelectronic technique to form more than one foot comprising the upper substrate material, wherein:

each foot has a width that varies through the height of the foot, such that the width decreases from the engraved bottom structuration layer surface to a midpoint of the height, and the width increases from the midpoint to the third substrate surface;

each foot is attached to the engraved bottom structuration layer surface of one or the engraved structuration layers, such that each of the plurality of the engraved structuration layers is attached to a single foot;

each foot is formed by engraving the uncovered area of the first substrate surface to the third substrate surface of the lower substrate layer; and each foot comprises a planar cross-section that is smaller than a planar cross-section of an engraved structuration layer to which it is attached;

(d) chemically functionalizing the engraved top structuration layer surface an upper face of each of the plurality of engraved structuration layers with one or more molecular components to obtain, on each of the plurality of engraved structuration layers, a monolayer comprising the one or more molecular components attached to the engraved top structuration layer surface, wherein each of the plurality of engraved structuration layers is chemically functionalized using a molecule printing technique selected from the group consisting of a microcontact printing, a dip-pen nanolithography and a polymer-pen lithography; and (e) breaking each foot by applying a controlled mechanical breaking load to each foot, thereby forming the plurality of chemically functionalized microparticles, wherein a rupture limit of the structuration material ($L_{STM}$) is greater than a rupture limit of the upper substrate material ($L_{UTM}$) according to the formula: ($L_{STM}$)/$L_{USM}$)>1; and wherein each chemically functionalized microparticle comprises:

a residual portion of the foot comprising the upper substrate material, wherein the residual portion comprises a planar cross-section that is smaller than the planar cross-section of the engraved structuration layer to which it is attached, and wherein the residual portion of each foot has a width that decreases in a direction from the engraved bottom structuration layer surface to a terminus of the residual portion;

the engraved structuration layer defining both geometry and lateral dimensions of a top surface of the chemically functionalized microparticle; and the monolayer comprising the one or more molecular components attached to the engraved top structuration layer surface of the engraved structuration layer.

2. The method according to claim 1, wherein the upper substrate material consists of a silicon sheet.

3. The method according to claim 1, wherein the structuration layer is prepared by a third microelectronics technique selected from the group consisting of thermal growth, chemical vapor deposition, sputtering and evaporation.

4. The method according to claim 1, wherein the engraving of the uncovered area of the upper substrate layer is carried out by a lateral physical etching or a lateral chemical etching.

5. The method according to claim 1, wherein the first microelectronic lithography technique is a photo-lithographic technique.

6. The method according to claim 1, wherein the one or more molecular components are selected from the group consisting of a peptide, a protein, a nucleotide, a nucleic acid, and any combination thereof.

7. The method according to claim 1, wherein the one or more molecular components comprise more than one different molecular component that is chemically functionalized on the engraved top structuration layer surface of each of the plurality of the engraved structuration layers.

8. The method according to claim 1, wherein the controlled mechanical breaking load comprises a technique selected from the group consisting of a rasping technique, a cutting technique, a cryofracturing technique, and an adhesive technique.

9. The method according to claim 8, wherein the controlled mechanical breaking load comprises:

applying an adhesive material to the monolayer to obtain a composite layer comprising the adhesive material, the monolayer, the engraved structuration layer, and a portion of the foot;

mechanically separating the composite layer from a remaining portion of the foot that is attached to lower substrate layer, to obtain a separated composite layer; and dissolving the adhesive material of the separated composite layer in a media to obtain the chemically functionalized microparticle.

10. The method of claim 1, wherein each of the chemically functionalized microparticles comprise a dimension from 1 micrometer (μm) to 100 μm.

11. The method of claim 1, wherein the monolayer comprises more than one of the molecular components.

12. The method of claim 1, wherein:
the planar cross-section of each foot is less than or equal to 50% of the planar cross-section of the engraved structuration layer to which each foot is attached; and
the planar cross-section of the residual portion of each chemically functionalized microparticle is less than or equal to 50% of the planar cross-section of the engraved structuration layer to which each of the residual portion is attached.

13. The method of claim 1, wherein the one or more molecular components comprise a single molecular component applied more than one time to the engraved top structuration layer surface of each of the plurality of the engraved structuration layers.

14. The method of claim 1, wherein the one or more molecular components comprises a polymer.

15. The method of claim 1, wherein the one or more molecular components comprises a peptide.

16. The method of claim 1, wherein the one or more molecular components comprises a protein.

17. The method of claim 1, wherein the one or more molecular components comprises a nucleotide.

18. The method of claim 1, wherein the one or more molecular components comprises a nucleic acid.

19. The method of claim 1, wherein the upper substrate material and the lower substrate material independently comprise at least one selected from the group consisting of a silicon, silicon nitride, silicon oxide, polycrystalline silicon, gold, platinum, aluminum, copper, nickel, cobalt, a metal oxide, a metal silicate and a metal silicide.

20. The method according to claim 8, wherein the controlled mechanical breaking load comprises a cryofracturing technique.

21. The method according to claim 1, wherein the engraving of the uncovered area of the shaped structuration layer, and the engraving of the uncovered area of the upper substrate layer, are carried out using different engraving techniques.

22. The method according to claim 2, wherein the upper substrate material comprises a monocrystalline silicon.

23. The method according to claim 19, wherein the structuration material comprises silicon oxide.

24. The method according to claim 23, wherein the engraving of the shaped structuration layer comprises vertically etching the uncovered area of the shaped structuration layer using a dry reactive ion etching with a mixture of ethane ($C_2H_6$) and trifluoromethane ($CHF_3$).

25. The method according to claim 23, wherein the engraving of the upper substrate layer comprises isotropic etching of the uncovered area of the upper substrate layer using a deep reactive ion etching (DRIE) with a mixture of sulfur hexafluoride ($SF_6$) and perfluorocyclobutane ($C_4F_8$); and the isotropic etching comprises laterally etching the uncovered area to form the plurality of feet.

* * * * *